(12) United States Patent
Gold

(10) Patent No.: US 6,187,343 B1
(45) Date of Patent: Feb. 13, 2001

(54) PROCEEDING FOR THE PREPARATION OF THE PROLONGED ACTION GRANULE COMPOUND CONTAINING 4-NITRO-2-PHENOXYMETHANESULFONANILIDE

(76) Inventor: Oscar Gold, San Martin 686, 7° floor "72", 1004 Buenos Aires (AR)

( * ) Notice: Under 35 U.S.C. 154(b), the term of this patent shall be extended for 0 days.

(21) Appl. No.: 08/996,174

(22) Filed: Dec. 22, 1997

(30) Foreign Application Priority Data

Jan. 2, 1997 (AR) .................................... P97-01-00002

(51) Int. Cl.$^7$ .................................................... A61K 9/58
(52) U.S. Cl. ......................... 424/487; 424/486; 424/488
(58) Field of Search .................................. 424/489, 487, 424/486, 488

(56) References Cited

U.S. PATENT DOCUMENTS

| | | | | |
|---|---|---|---|---|
| 5,547,683 | * | 8/1996 | Yano et al. ........................... | 424/501 |
| 5,622,716 | * | 4/1997 | Barth .................................... | 424/461 |
| 5,711,961 | * | 1/1998 | Reiner et al. ........................ | 424/441 |
| 5,744,165 | * | 4/1998 | Geczy ................................... | 424/499 |
| 5,756,546 | * | 5/1998 | Pirotte et al. ........................ | 514/605 |

OTHER PUBLICATIONS

C.A.114:128992 W.K. Cheung et al. J. Pharm. Sci. (1991) 80(2) 142–8.*

* cited by examiner

Primary Examiner—Peter F. Kulkosky
(74) Attorney, Agent, or Firm—Pendorf & Cutliff

(57) ABSTRACT

The invention includes a compound formulated by means of an association of sustained liberation in granules that maintains the therapeutic action of 4-nitro-2-phenoxymethanesulfonanilide and with a decrease of the fluctuations of the plasmatic concentrations the invention also includes a proceeding to obtain the compound. The active agent is micronized together with a disintegrant and adhered by means of bonding polymers from a solution to neutral granules made of sugar, forming granules of fast, conventional or immediate action. A fraction of the granules adhered and coated with the active agent is incorporated to polymers from a solution that confer a prolonged and controlled action to the active agent and is associated or mixes to the remaining granules containing the active agent (granules of immediate action), to prepare and administer different doses.

16 Claims, 2 Drawing Sheets

Figure 1:
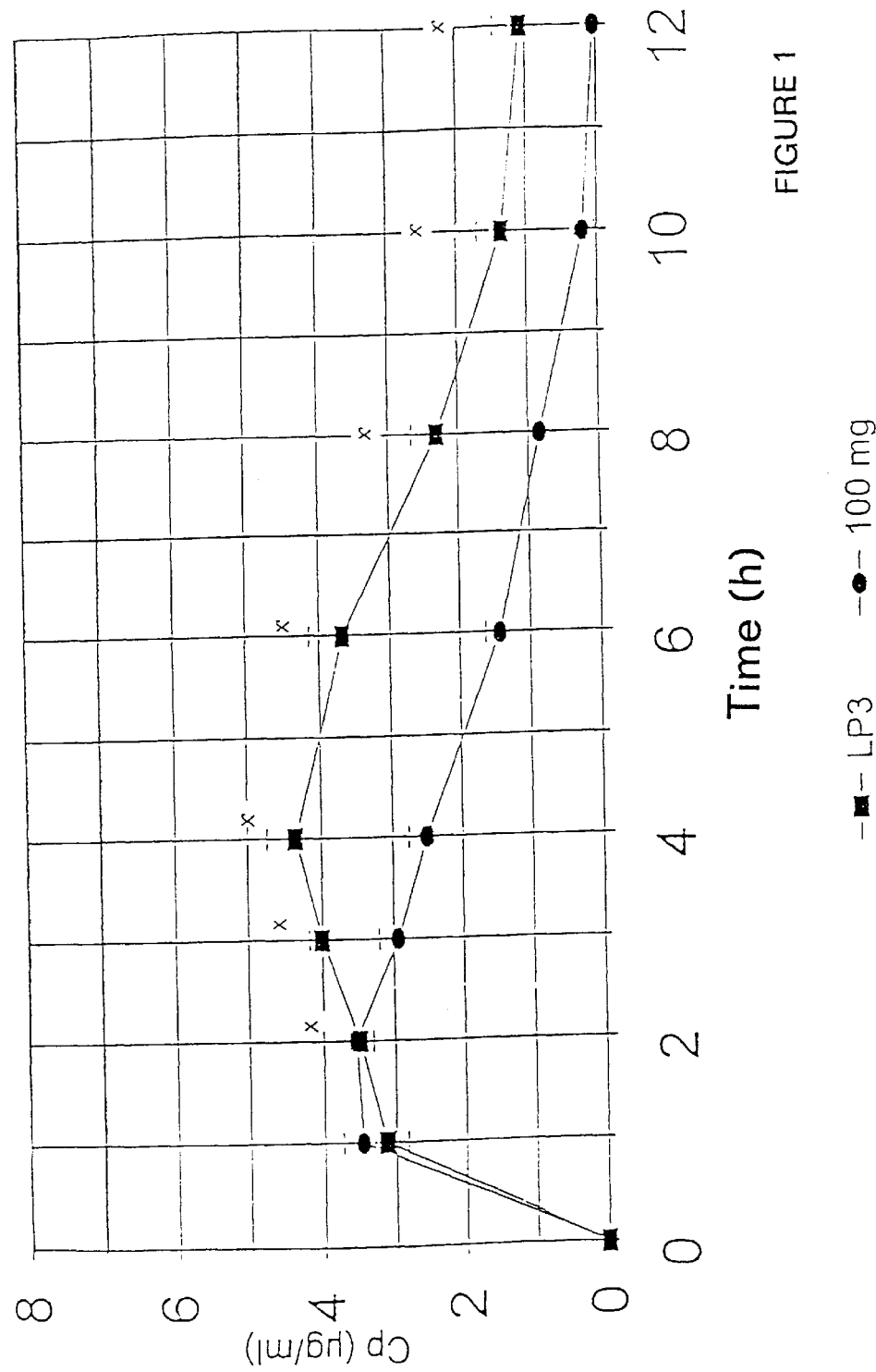
Figure 2:
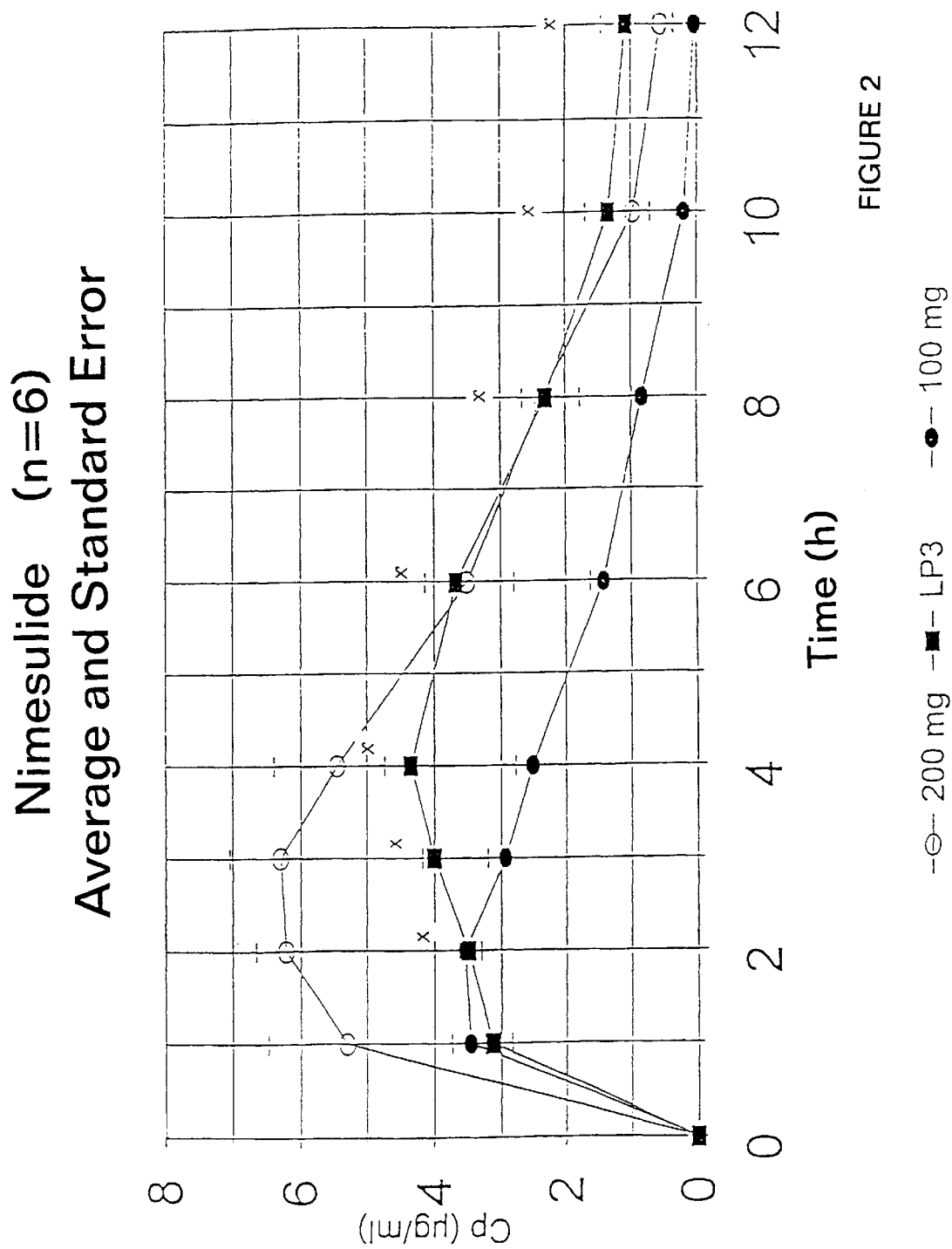

PROCEEDING FOR THE PREPARATION OF THE PROLONGED ACTION GRANULE COMPOUND CONTAINING 4-NITRO-2-PHENOXYMETHANESULFONANILIDE

FIELD OF THE INVENTION

The present invention refers to a proceeding to formulate a compound of sustained and prolonged liberation in the form of granules that maintains the therapeutic action of 4-nitro-2-phenoxymethanesulfonanilide and with a decrease in the fluctuations of plasmatic concentration. This active principle 4-nitro-2-phenoxymethanesulfonanilide is nowadays employed as a medicine sold under the trademark "NIMESULIDE".

It is a non-steroid anti-inflammatory agent with anti-inflammatory, analgesic and anti-pyretic action indicated for (osteoarthritis, rheumatoid arthritis, chronical inflammatory states of the superior respiratory tract, inflammation of the otolaryngologycal sphere, soft tissues, genital-urinary tract, dysmenorrhea, thrombophlebitis, phlebitis, odontalgia) with adverse effects of the digestive type.

PRIOR ART

Nimesulide or 4-nitro-2-phenoxymethanesulfonanilide, is known since 1974 from the Belgian patent n. 804,812 and U.S. Pat. No. 3,840,897. Both patents define Nimesulide in its preparation and anti-inflammatory activity.

The presentation of the product is in 100 mg and 200 mg compounds of fast or conventional action, There are other non-steroid anti-inflammatories in the world market, with which it was demonstrated that the forms of programmed and sustained action of continuous liberation, compared to the administration of the same product in its conventional form have less incidence of secondary effects, for example, we have Sodium Diclofenac, Ketoprofen, Indometacine, etc., the forms sustained in continuous liberation granules being in most cases the most secure, efficient and maintaining the plasmatic levels within the therapeutic ranges.

SUMMARY OF THE INVENTION

The present invention, according to the exposed, is a proceeding related to a preparation of controlled liberation of 4-nitro-2-phenoxymethanesulfonanilide (active agent) in multiple granules that liberate gradually the active agent and maintains stable plasmatic concentrations.

The object of the present invention is to achieve an association of this active agent allowing more stable plasmatic concentrations and reducing secondary effects of the digestive type.

This invention of granules or micro-granules containing 4-nitro-2-phenoxymethanesulfonanilide includes:

1. Neutral granules or neutral micro-granules composed of sugar and starch.

2. Incorporation and adherence of the powder-like micronized active agent that adheres to the neutral micro-granules by means of some bonding polymers provided by the solution giving as a result granules commonly denominated fast-action granules, conventional or immediate, and separating the resulting granules into two portions.

3. Adherence of some polymers that form a film form a solution containing them with which a fraction (one portion) of the product of a previous stage is covered, obtaining granules of active principle of sustained and controlled action.

4. Association or mixing of the non-covered granules in 2 with the granules of 3.

The neutral granules are 0.2 mm to 1.8 mm in size, preferably 0.4 mm to 1.4 mm.

According to preferred characteristics of the invention, the active agent is associated to a disintegrator mixed, as a step previous to micronization. The disintegrator may be sodium croscaramellose or crospovidone or other.

The solvents used in 2 for the adherent solution may be acetone, isopropylic alcohol, water or their mixture.

The bonding polymers may be different types of polyvinylpyrrolidines or polyethylene glycols, jellies or their mixtures.

Once the active principle is incorporated and the granules dried, to one part of the same a solution of polymers is added, which gives a sustained and controlled action to the active principle and that form a coating over the granules once the same are dry.

The solvents used may be acetone, isopropylic alcohol, water or their mixtures.

The coating polymers used for giving the sustained and controlled action may be different types of methyl celluloses, different types of hydroxypropylrnethyl celluloses, different types of phthalate of hydroxypropylmethyl celluloses, different types of acrylic polymers (which can be different types of Eudragit L, Eudragit S, Eudragit RL or Eudragit RS or their combinations), different types of shellac and different types of ethyl celluloses; all these polymers may be combined in different proportions.

To this solution it is possible to incorporate plastifiers such as diethylphthalate, dibutylphthalate, polyethylene glycol, triethyl citrate, triacetin, triglycerids of fatty acids, or others.

It is preferable the adding of a lubricant before the drying process, commonly silicon dioxide.

According to other characteristics of the invention the following proportions are preferable for 2.

The proportion of the active principle respecting the rest of the excipients must be between 20% and 90%, and the one of bonding polymers with respect to the rest of the excipients between 0.2% and 5% of disintegrants between 0.5% and 7%.

It is also preferable that the final concentration of granules of active principle to be between 20% and 80% and the size of the granules to be between 0.6 mm and 2 mm, preferably between 0.8 mm and 1.7 mm.

The proportion of acrylic polymers respecting the rest of the polymers may be between 0% and 100%.

The solvent used in the phases 2 and 3 may be 0% to 100% organic or 0% to 100% aqueous.

The final proportion of granules from 2 with respect to the final mixture may be 0% to 50%.

The granules containing 4-nitro-2-phenoxymethanesulfonanilide make possible the preparation and administration of different doses, due to this they may be dosed in capsules of hard jelly in different concentrations.

The association in granules of active principle has a programmed and sustained dissolution system that can be controlled with the Dissolution Equipment USP-type XXIII, page 1791 of the basket type at 100 r.p.m. and each glass with 500 ml of digestive solution, realizing the change in pH in the different hour fractions.

The profile of the solution is the following:

| | | |
|---|---|---|
| 1st hour | 20% | 50% |
| 4th hour | 55% | 85% |
| 8th hour | | >80% |

With this invention one can achieve ways of giving doses of 4-nitro-2-phenoxymethanesulfonanilide of prolonged and sustained action with stable hematic concentrations.

EXAMPLES

The invention is further defined by means of the following examples:

Example 1

| | |
|---|---|
| Neutrals | 120 g |
| Sodium croscaramellose | 8 g |
| Polyvinylpyrrolidine | 4 g |
| Phthalate hydroxypropylmethyl cellulose | 85 g |
| Eudragit RL | 50 g |
| Shellac | 95 g |
| Triethylcitrate | 16 g |
| Active principle | 615 g |

1. In a double-cone mixer the active principle and the sodium croscaramellose are mixed; this association is micronized to a size inferior to 40 micras.

2. The resulting powder in 1 is incorporated slowly to a stainless steel pan that rotates at a speed between 8 and 30 r.p.m. in which the neutral granules have already been incorporated.

The adding of the micronized material is simultaneous to the atomization of a solution over the neutrals; said solution is of polyvinylpyrrolidine in isopropylic alcohol. (4 g solute–36 g solvent)

Once the process is finished the product is left to dry.

3. From the resulting product 35% of 2 is separated in weight and the 65% left is coated in a pan that works at a speed between 8 and 30 r.p.m., atomizing over the granules in order to coat them with a solution containing solutes (phthalate hydroxypropylmethyl cellulose, Eudragit RL, shellac, triethylcitrate) (246 g) dissolved in (1.400 g) of solvent with the proportion of 50% isopropylic alcohol, 40% acetone and 10% water.

4. The product resulting in 3 is dried, previously silicon dioxide is added and is mixed with the granules from 2.

Example 2

| | |
|---|---|
| Neutrals | 120 g |
| Crospovidone | 11 g |
| Polyethylene glycol | 3 g |
| Phthalate hydroxypropylmethyl cellulose | 45 g |
| Hydroxypropylmethyl cellulose | 52 g |
| Eudragit RS | 27 g |
| Ethylcellulose | 50 g |
| Triacetin | 10 g |
| Silicon dioxide | 4 g |
| Active principle | 675 g |

1. In a double-cone mixer the active principle and the crospovidone are mixed; this association is micronized to a size inferior to 40 micras.

2. The resulting powder in 1 is incorporated slowly to a stainless steel pan that rotates at a speed between 8 and 30 r.p.m. in which the neutral granules have already been incorporated.

The adding of the micronized material is simultaneous to the atomization of a solution over the neutrals; said solution is of polyethylene glycol in water. (3 g solute–10 g solvent)

Once the process is finished the product is left to dry.

3. From the resulting product 30% of 2 is separated in weight and the 70% left is coated in a pan that works at a speed between 8 and 30 r.p.m., atomizing over the granules in order to coat them with a solution containing solutes (phthalate hydroxypropylmethyl cellulose, Eudragit RS, ethyl cellulose, triacetin) (184 g) dissolved in (1.200 g) of solvent with the proportion of 70% isopropylic alcohol, 25% acetone and 50% water.

4. The product resulting in 3 is dried, previously silicon dioxide is added and is mixed with the granules from 2.

Example 3

| | |
|---|---|
| Neutrals | 120 g |
| Sodium croscaramellose | 4 g |
| Crospovidone | 5 g |
| Polyvinylpyrrolidine | 5 g |
| Phthalate hydroxypropylmethyl cellulose | 30 g |
| Eudragit RL | 30 g |
| Eudragit L | 29 g |
| Shellac | 110 g |
| Dibutylphtalate | 8 g |
| Silicon dioxide | 2 g |
| Active agent | 608 g |

1. In a double-cone mixer the active principle, sodium croscaramelose and crospovidone are mixed; this association is micronized to a size inferior to 40 micras.

2. The resulting powder in 1 is incorporated slowly to a stainless steel pan that rotates at a speed between 8 and 30 r.p.m. in which the neutral granules have already been incorporated.

The adding of the micronized material is simultaneous to the atomization of a solution over the neutrals; said solution is of polyvinylpyrrolidine in isopropylic alcohol. (5 g solute–40 g solvent)

Once the process is finished the product is left to dry.

3. From the resulting product 42% of 2 is separated in weight and the 58% left is coated in a pan that works at a speed between 8 and 30 r.p.m., atomizing over the granules in order to coat them with a solution containing solutes (phthalate hydroxypropylmethyl cellulose, Eudragit RL, Eudragit L shellac, dibutylphthalate) (207 g) dissolved in (1.500 g) of solvent with the proportion of 75% isopropylic alcohol, 20% acetone and 5% water.

4. The product resulting in 3 is dried, previously silicon dioxide is added and is mixed with the granules from 2.

Example 4

| | |
|---|---|
| Neutrals | 120 g |
| Sodium Croscaramellose | 10 g |
| Polyvinylpyrrolidine | 3 g |
| Eudragit RS | 25 g |
| Eudragit L | 60 g |

-continued

| | |
|---|---|
| Eudragit S | 10 g |
| Shellac | 70 g |
| Ethyl cellulose | 15 g |
| Triacetin | 3 g |
| Triethylcitrate | 14 g |
| Silicon dioxide | 3 g |
| Active agent | 620 g |

1. In a double-cone mixer the active agent and sodium croscaramellose are mixed; this association is micronized to a size inferior to 40 micras.

2. The resulting powder in 1 is incorporated slowly to a stainless steel pan that rotates at a speed between 8 and 30 r.p.m. in which the neutral granules have already been incorporated.

The adding of the micronized material is simultaneous to the atomization of a solution over the neutrals; said solution is of polyvinylpyrrolidine in isopropylic alcohol and acetone. (5 g solute–40 g solvent 95% isopropylic alcohol and 5% acetone)

Once the process is finished the product is left to dry.

3. From the resulting product 33% of 2 is separated in weight and the 67% left is coated in a pan that works at a speed between 8 and 30 r.p.m., atomizing over the granules in order to coat them with a solution containing solutes (, Eudragit RS, Eudragit S, Eudragit L, shellac, ethyl cellulose, triacetine triethylcitrate) (197 g) dissolved in (1.500 g) of solvent with the proportion of 50% isopropylic alcohol, 40% acetone and 10% water.

4. The product resulting in 3 is dried, previously silicon dioxide is added and is mixed with the granules from 2.

Example 5

| | |
|---|---|
| Neutrals | 120 g |
| Sodium croscaramellose | 10 g |
| Polyvinylpyrrolidone | 4 g |
| Phthalate hydroxypropylmethyl cellulose | 95 g |
| Eudragit RL | 60 g |
| Shellac | 87 g |
| Triethylcitrate | 14 g |
| Silicon dioxide | 5 g |
| Active agent | 608 g |

1. In a double-cone mixer the active agent and sodium croscaramellose are mixed; this association is micronized to a size inferior to 40 micras.

2. The resulting powder in 1 is incorporated slowly to a stainless steel pan that rotates at a speed between 8 and 30 r.p.m. in which the neutral granules have already been incorporated.

The adding of the micronized material is simultaneous to the atomization of a solution over the neutrals; said solution is of polyvinylpyrrolidine in isopropylic alcohol. (4 g solute–14 g solvent)

Once the process is finished the product is left to dry.

3. From the resulting product 35% of 2 is separated in weight and the 70% left is coated in a pan that works at a speed between 8 and 30 r.p.m., atomizing over the granules in order to coat them with a solution containing solutes (phthalate hydroxypropylmethyl cellulose, Eudragit RL, shellac, triethylcitrate) (256 g) dissolved in (2.300 g) of solvent with the proportion of 85% isopropylic alcohol, 11% acetone and 4% water.

4. The product resulting in 3 is dried, previously silicon dioxide is added and is mixed with the granules from 2.

The Test of Liberation of the granules was effected according to U.S.P. XXIII, basket method with 500 ml glass changing the pH in hourly fractions obtaining the following results:

| | Liberation Percentage | | | | |
|---|---|---|---|---|---|
| Hs | Example 1 | Example 2 | Example 3 | Example 4 | Example 5 |
| 1 | 35 | 31 | 43 | 34 | 40 |
| 4 | 76 | 72 | 80 | 70 | 77 |
| 8 | 95 | 91 | 99 | 91 | 98 |

Pharmacokinetical Studies

Bearing in mind the abovementioned and the example presented, capsules with granules or microgranules of 200 mg 4-nitro–2-phenoxymethanesulfonanilide of controlled action were produced, and comparative pharmacokinetic studies were with the sold products of conventional action with a dosage of 100 mg and 200 mg.

As significant parameters the maximum plasmatic concentration (Cmax), the time to reach the maximum concentration (Tmax) and the area under the curve (AUC) was calculated in each one of the products. The studies were done with 6 individuals for each one of the 3 products which were administered with a dose orally and extractions were effected at different hours, analyzing the plasmatic concentrations, and realizing the statistical study of the calculated parameters.

All along the evaluation, the products are defined in the following way:

LP3 microgranules of prolonged or controlled action of 4-nitro–2-phenoxymethanesulfonanilide in hard jelly capsules with a 200 mg dose.

100 mg 100 mg dose of Nimesulide in tablets of conventional action.

200 mg 200 mg dose of Nimesulide in tablets of conventional action.

The characteristics to be considered in relation to the prolonged action product with respect to the 100 mg and 200 mg conventional products are the following:

the LP3 product has plasmatic levels compared with the 100 mg product which are similar during the first three hours but are more stable and superior in the following hours. With respect to the 200 mg. product it has plasmatic concentrations which are more stable and superior during the first 5–6 hours maintaining similar levels in the following hours.

The LP3 product with these characteristics is defined as of controlled action and it is demonstrated in Table I and FIGS. I and II enclosed herein, observing a significant shift of Tmax, and Cmax and a AUC with no significant differences respecting the 200 mg product and at the same time with concentrations which are stable through the hours.

Table I and FIGS. I and II show the parameters of granules of 4-nitro-2-phenoxymethanesulfonanilide, conventional Nimesulide 100 mg. and conventional Nimesulide 200 mg. (average values of 6 individuals). In the enclosed graphs:

FIG. 1 shows the average concentrations along the time of granules 4-nitro-2-phenoxymethanesulfonanilide and Nimesulide 100 mg (average values of 6 individuals) while, FIG.

2 shows average concentrations along the time of granules of 4-nitro-2-phenoxymethanesulfonanilide, conventional Nimesulide 100 mg and conventional Nimesulide 200 mg(average value of 6 individuals).

TABLE I

| Formulation | Cmax ug/ml | Tmax (hours) | AUC (ug · h/ml) | F (LP3/ conventional dose) |
|---|---|---|---|---|
| LP3 | 4.6 ± 0.328 | 3.7 ± 0.211 | 37.1 ± 3.17 | — |
| 100 mg | 3.8 ± 0.122 | 1.5 ± 0.342 | 20.0 ± 1.73 | 0.93 ± 0.063 |
| 200 mg | 7.5 ± 0.389 | 1.8 ± 0.543 | 42.6 ± 5.06 | 0.90 ± 0.066 |

The present invention has been thus described as an example in order to allow the skilled in the art to understand and carry out the fundaments of the invention, but it is indubitable that modifications can be produced without parting form the spirit and scope of the invention.

What is claimed is:

1. A method for preparing a compound of granules of prolonged action containing 4-nitro-2-phenoxymethanesulfonanilide as active agent characterized by the following steps:
   i) mixing the active agent of fast action granules with a disintegrant;
   ii) micronizing the active agent together with a disintegrant;
   iii) rotating the micronized active agent disintegrant mix in a pan containing neutral granules simultaneously with the atomization of a solution of bonding polymers selected from a solution consisting of jellies of polyvinylpyrrolidine, polyethylene glycols or mixtures thereof to form granules of intermediate or conventional action;
   iv) separating the granules into two portions by weight with the one portion having the lower weight of the intermediate or conventional action granules and being removed from the pan with only the coating of the solution of the bonding polymers;
   v) atomizing coating polymers from a solution consisting of cellulose, acrylic polymers, shellac or combination thereof, and a plasticizer over one other of the two portions, having the greater weight and remaining in the pan, to form granules of controlled and prolonged action of the active principle having a granule size between 0.6 mm to 2.0 mm; and
   vi) associating or mixing the immediate or conventional action granules with the granules of controlled and prolonged action polymers to allow the preparation of a compound of sustained and prolonged liberation for administration of different doses of the active agent.

2. The method according to claim 1 wherein the neutral granules have a size ranging from 0.4 mm to 1.4 mm.

3. The method according to claim 2 wherein:
   (A) the bonding polymer that adheres to the micronized active agent to form the intermediate or conventional portion is a polyvinylpyrrolidones in a solvent; and
   (B) the coating polymers atomized over the other portion forming the granules of controlled and prolonged action of the active principle consisting of, phthalate hydroxypropylmethyl cellulose, shellac, acrylic polymers selected from the group of methacrylates consisting of Eudragit L or Eudragit RL or combination thereof, and a plastifier.

4. The method according to claim 3 wherein the active agent is mixed with disintigrants selected from the group consisting of sodium croscaramelose, crospovidone, alone or combined.

5. The method according to claim 3 wherein the percentage of granules of immediate action in the mixture or association with the granules of prolonged and controlled action varying from 30 to 45 %.

6. The method according to claim 3 wherein the solvents used in (ii) and (iii) are selected from the group consisting of acetone, isopropylic alcohol, water, alone or combined.

7. The method according to claim 3 wherein the plasticizers are selected from a group consisting of diethylphthalate, polyethylene glycol, dibutylphthalate, triacetin, triethylcitrate, triglycerides of fatty acids alone or combined.

8. The method according to claim 3 wherein the ratio of active principle to the excipients must be between 50% and 70%.

9. The method according to claim 3 wherein the ratio of bonding polymers to the excipients is between 0.5% and 1.4%.

10. The method according to claim 3 wherein the ratio of disintegrants is between 2.0% and 4.0%.

11. The method according to claim 4 wherein the percentage of methacrylates in proportion with the bonding polymers and coating polymers is between 10% and 50%.

12. The method according to claim 3 wherein the final size of the granules is in the range of 0.8 mm and 1.7 mm.

13. The method according to claim 1 wherein the granules maintain stable plasmatic concentrations during the first 5–6 hours while doses of greater concentration when given are less stable in maintaining plasmatic concentrations during the corresponding time period.

14. The method according to claim 3, wherein the methacrylates are chosen from the group of acrylic polymers consisting of Eudragit L and Eudragit RL or combinations thereof.

15. The method according to claim 7 further including the steps of:
   preparing doses of the granules to maintain stable plasmatic concentrations corresponding to the plasmatic concentrations maintained when doses of less concentration are given during 3 hours, with the prepared dose of the granules having a maximum plasmatic concentration of approximately 4.2 to 5.0 hours after ingestion and maintaining stable plasmatic concentrations beyond 5 hours while doses of less concentration provide less stable plasmatic concentrations.

16. The method according to claim 15 further including the steps of:
   preparing doses of the granules to maintain stable plasmatic concentrations during the first 5–6 hours after the doses while doses of greater concentration when given are less stable in maintaining plasmatic concentrations during the corresponding time period.

* * * * *